United States Patent [19]

Umemura et al.

[11] 4,290,922
[45] Sep. 22, 1981

[54] AMMOXIDATION CATALYST FOR THE PRODUCTION OF ACRYLONITRILE FROM PROPYLENE AND PROCESS FOR PRODUCING THE SAME

[75] Inventors: Sumio Umemura; Kyoji Ohdan; Mikio Hidaka; Toshio Kurafuji, all of Ube, Japan

[73] Assignee: Ube Industries, Ltd., Yamaguchi, Japan

[21] Appl. No.: 134,053

[22] Filed: Mar. 26, 1980

[30] Foreign Application Priority Data

Apr. 18, 1979 [JP]  Japan .................. 54/46728

[51] Int. Cl.$^3$ ............. B01J 21/06; B01J 23/24
[52] U.S. Cl. ................... 252/456; 252/458; 252/459; 260/465.3
[58] Field of Search ............ 252/451, 456, 458, 459; 260/465.3

[56] References Cited

U.S. PATENT DOCUMENTS

| | | | |
|---|---|---|---|
| 4,035,418 | 7/1977 | Ikada et al. .................. | 252/456 |
| 4,148,757 | 4/1979 | Brazdil et al. ................ | 252/458 |
| 4,212,766 | 7/1980 | Brazdil et al. ................ | 260/465.3 |

FOREIGN PATENT DOCUMENTS 2523983  11/1975  Fed. Rep. of Germany ... 260/465.3

*Primary Examiner*—G. O. Peters
*Attorney, Agent, or Firm*—Burgess, Ryan and Wayne

[57] ABSTRACT

A catalyst for the ammoxidation of propylene to prepare acrylonitrile with a high yield thereof comprising an oxide composition of the empirical formula (I)

$$Mo_a Co_b Ni_c Fe_d Bi_e V_f Ca_g K_h X_i Si_j O_k \qquad (I)$$

wherein X is zirconium and/or chromium, the subscripts a, b, c, d, e, f, g, h, i and j respectively denote the number of the respective atoms of the elements, when a=10, b=0 to 8, c=0 to 8, (b+c)=2 to 10, d=0.3 to 7, e=0.01 to 3, f=0.01 to 2, g=0.01 to 5, h=0.05 to 0.5, i=0 to 2, j=10 to 50, and the subscript k denotes the number of oxygen atoms which satisfies the average valency of the elements other than oxygen and the ratio a:k being in a range of 10:30 to 80, which catalyst is prepared by preparing an aqueous slurry containing respective element-containing compounds, by spray drying the aqueous slurry to prepare a dried solid precursory catalyst and, finally, by calcining the precursory catalyst as a temperature of from 500° to 750° C. to provide an activated catalyst.

8 Claims, No Drawings

4,290,922

AMMOXIDATION CATALYST FOR THE PRODUCTION OF ACRYLONITRILE FROM PROPYLENE AND PROCESS FOR PRODUCING THE SAME

FIELD OF THE INVENTION

The present invention relates to an ammoxidation catalyst for the production of acrylonitrile from propylene and a process for producing such a catalyst. More particularly, the present invention relates to an ammoxidation catalyst which is useful for the production of acrylonitrile from propylene and which exhibits excellent mechanical strength, especially an excellent resistance to attrition, and a process for producing such a catalyst.

BACKGROUND OF THE INVENTION

It is known that acrylonitrile can be produced from propylene in various processes in which propylene is brought into contact with molecular oxygen and ammonia in a gas phase in the presence of a catalyst at an elevated temperature. These processes are known as catalytical ammoxidation processes for propylene. This ammoxidation of propylene can be effected only in the presence of a catalyst. U.S. Pat. No. 2,904,580 disclosed, for the first time, a P—Mo—Bi—O type catalyst effective for the ammoxidation of propylene. After this U.S. patent, various types of catalysts were provided for the ammoxidation process for propylene. For example, U.S. Pat. No. 3,766,092 discloses an Mo—Bi—Fe—Co—Na and/or K—P—O type ammoxidation catalyst; British Patent No. 1,319,190 discloses an [(Ni and/or Co)—(As and/or P)—Fe—Bi—Mo—(Alkalimetal, Ta, Nb and/or rare earth metal)—O] type ammoxidation catalyst; U.S. Pat. No. 4,123,453 discloses an [(alkali metal)—(Ni and/or Co)—(As and/or P)—(at least one element selected from Groups IIA and IIB in the Periodic Table)—Fe—Bi—Mo—O] type ammoxidation catalyst; British Pat. No. 1,478,621 discloses an X—(A)—C—Fe—Bi—Mo—O type ammoxidation catalyst in which X denotes at least one member selected from the group consisting of Ge, Sn, Cu, Ag, Cr, Ru, W, Be, B, Ga, In, Mn, Sb, Th, Zr and Y, A denotes at least one element selected from the group consisting of alkali metals, alkaline earth metals, rare earth elements, Nb, Ta, Tl, P and As and C represents at least one element selected from the group consisting of Co, Mg, Zn, Cd and Ca, and; U.S. Pat. No. 3,872,148 discloses a [Bi—Mo—W—(at least one element selected from Group II in the Periodic Table)—(at least one element selected from the group consisting of Ti, Zr, Nb, Ta, V, Cr, Mn, Fe, Co and Ni)—O] type ammoxidation catalyst.

Some of the above-mentioned conventional ammoxidation catalysts are effective for producing acrylonitrile with a high yield. However, almost all of the conventional ammoxidation catalysts are industrially unsatisfactory due to their poor resistance to attrition. It is essential that industrially usable catalysts exhibit a high resistance to attrition.

In order to enhance the resistance of the catalyst to attrition, it is effective to utilize a carrier consisting of for example, silica. However, usually, the utilization of a carrier results in a remarkable decrease in the yield of acrylonitrile. That is, when a carrier is used in such an amount that the resistance of the catalyst to attrition is considerably enhanced, the yield of acrylonitrile is significantly reduced.

When a conventional catalyst, which is effective for producing acrylonitrile with a high yield but which exhibits a poor resistance to attrition, is used in a fixed bed type reactor, the charging operation of the catalyst into the reactor causes the catalyst to be abraded and pulverized. The pulverized catalyst particles hinder the flow of reaction gases through the reactor. This hindering results in an undesirable increase in the pressure drop through the reactor and in side-reactions.

Also, when a conventional catalyst is used in a fluidized bed type reactor, during the ammoxidation reaction, the catalyst is abraded and pulverized during the time the reaction is taking place. A portion of the pulverized catalyst particles flow out with the reaction gases from the reactor. The loss of the catalyst from the reactor causes the fluidized bed reaction to become unstable and the life of the catalyst to be shortened. In this case, accordingly, it is necessary to feed an additional amount of the catalyst to the reactor, which additional amount corresponds to the loss of the catalyst. Therefore, the yield of acrylonitrile per unit amount of the catalyst decreases.

Accordingly, it is strongly desired to provide an ammoxidation catalyst which is effective for producing acrylonitrile with a high degree of selectivity to acrylonitrile with a high yield of acrylonitrile and which exhibits excellent resistance to attrition. Furthermore, in order to reduce the cost of the catalyst, it is desired that, even when the catalyst is borne on a large amount of the carrier, the catalyst is capable of producing acrylonitrile with a high yield at a relatively low temperature in a relatively short contact time.

SUMMARY OF THE INVENTION

An object of the present invention is to provide an ammoxidation catalyst for the production of acrylonitrile from propylene, which catalyst exhibits an excellent resistance to attrition, and a process for producing such a catalyst.

Another object of the present invention is to provide an ammoxidation catalyst for the production of acrylonitrile from propylene, with a high degree of selectivity to acrylonitrile with a high yield of acrylonitrile, even at a relatively low temperature, and in a relatively short contact time, and a process for producing such a catalyst.

Another object of the present invention is to provide an ammoxidation catalyst for the production of acrylonitrile from propylene with a high degree of selectivity to acrylonitrile with a high yield of acrylonitrile, even when the catalyst is borne on a carrier consisting of, for example, silica, and a process for the production of the catalyst.

Another object of the present invention is to provide an ammoxidation catalyst for the production of acrylonitrile from propylene with a high degree of selectiveity to acrylonitrile with a high yield of acrylonitrile, even when the catalyst is borne on a carrier consisting of, for example, silica, and a process for the production of the catalyst.

The above-described objects can be attained by the ammoxidation catalyst of the present invention, which comprises an oxide composition of the empirical formula (I):

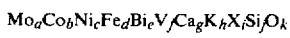

$$Mo_aCo_bNi_cFe_dBi_eV_fCa_gK_hX_iSi_jO_k \quad (I)$$

wherein X represents at least one element selected from the group consisting of zirconium and chromium, the subscripts a, b, c, d, e, f, g, h, i and j respectively denote the number of the respective atoms of the elements, and the ratio a:b:c:d:e:f:g:h:i:j is in a range of 10:0 to 8:0 to 8:0.3 to 7:0.01 to 3:0.01 to 2:0.01 to 5:0.05 to 0.5:0 to 2:10 to 50, the ratio a:(b+c) being in a range of 10:2 to 10, and the subscript k denotes the number of oxygen atoms which satisifies the average valency of the elements other than oxygen, the ratio a:k being in a range of 10:30 to 80.

The above-mentioned ammoxidation catalyst can be produced by the process of the present invention, which process comprises the steps of:

mixing an aqueous liquid with a molybdenium-containing compound, with at least one member selected from cobalt- and nickel-containing compounds, an iron-containing compound, a bismuth-containing compound, a vanadium-containing compound, a calcium-containing compound, a potassium-containing compound, with at least one member selected from zirconium- and chromium-containing compounds, and a silicon-containing compound, each in an amount sufficient to satisfy the above-specified atomic ratio of the elements in the empirical formula (I), to prepare an aqueous slurry, said aqueous slurry containing not more than 15% of the sum of the respective element-containing compounds which are in the form of solid particles having a size of 2 microns or less, based on the entire weight of said aqueous slurry, and having a pH of 1.0 or less;

converting the resultant aqueous slurry into a dried solid precursor catalyst by means of spray drying, and;

calcining said precursor catalyst at a temperature of from 500° to 750° C. to prepare an activated catalyst.

DETAILED DESCRIPTION OF THE INVENTION

It is essential that the ammoxidation catalyst of the present invention comprises an oxide composition of the empirical formula (I)

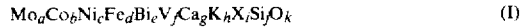

$$Mo_aCo_bNi_cFe_dBi_eV_fCa_gK_hX_iSi_jO_k \quad (I)$$

wherein X represents at least one element selected from the group consisting of zirconium and chromium, the subscripts a, b, c, d, e, f, g, h, i and j respectively denote the number of the respective atoms of the elements, when a=10, b=0 to 8; c=0 to 8; (b+c)=2 to 10, preferably, 3 to 9; d=0.3 to 7, preferably, 0.5 to 5; e=0.01 to 3, preferably, 0.03 to 2; f=0.01 to 2, preferably, 0.01 to 1; g=0.01 to 50, preferably, 0.05 to 4; h=0.05 to 0.5, preferably, 0.07 to 0.4; i=0 to 2, preferably, 0.1 to 1.9; and; j=10 to 50, preferably, 15 to 45, and the subscript k denotes the number of oxygen atoms which satisifies the average valency of the elements other than oxygen, when a=10, and k=30 to 80.

The catalyst of the present invention contains silicon, which is effective as a carrier, in a very large amount of from 10 to 50 atoms per 10 atoms of molybdenum. When the silicon is contained, in a catalyst, in an amount of 37 atoms per 10 atoms of molybdenum, the amount of silicon in terms of $SiO_2$ corresponds to about 50% of the entire weight of the catalyst. However, in spite of the fact that the silicon is contained in the above-mentioned large amount, the catalyst of the present invention is capable of ammoxidizing, in a fixed bed type reactor, propylene into acrylonitrile at a relatively low temperature of about 420° c. in a relatively short contact time of about 1.7 seconds, with an excellent conversion of propylene of about 100%, with an excellent selectivity of about 85% and with an excellent yield of about 85%. The catalyst of the present invention exhibits not only the above-mentioned advantages, but also, such an excellent resistance to attrition that when the catalyst is charged into the fixed bed type reactor, substantially no attrition and pulverization are observed.

The above-mentioned advantages can be found not only in the fixed bed type reactor, but also, in a fluidized bed type reactor.

In the catalyst of the present invention, it is not completely clear in what form of a compound, each of the molybdenum; cobalt and/or nikel; iron; bismuth; vanadium; calcium; potassium; zirconium and/or chromium, and silicon, exists, and what effect each element exhibits. However, it is correct that when the atomic ratios of the respective elements to each other fall in the outside of the specified range of the present invention, it becomes impossible to attain the objects of the present invention. Therefore, it is believed that all elements in the catalyst of the present invention are closely related to each other to contribute to the catalytic activity and mechanical properties of the catalyst. However, it is difficult to make clear the contribution of each element to the catalytic activity and mechanical properties of the catalyst.

Generally, it has been found by the inventors of the present invention, the cobalt and/or nickel in an amount of more than 8 atoms per 10 atoms of molybdenum causes the degree of selectivity to acrylonitrile to be poor and the resistance of the catalyst to attrition to be unsatisfactory. When the sum of cobalt and nickel is in an amount of less than 2 atoms per 10 atoms of molybdenum, the degree of reactivity of propylene is poor. Also, when the amount of iron is less than 0.3 atoms or more than 7 atoms per 10 atoms of molybdenum, the degree of selectivity to acrylonitrile is poor. Furthermore, when bismuth, vanadium, potassium and zirconium and/or chromium are respectively used in amounts outside the specified ranges of the present invention, either one or both of the degrees of conversion of propylene and selectivity to acrylonitrile are reduced and, therefore, the degree of yield of acrylonitrile becomes poor. Silicon and calcium, especially, silicon, are highly contributive to the resistance of the catalyst to attrition. Accordingly, when silicon and calcium are used in the amounts as specified by the present invention, the resultant catalyst exhibits excellent resistance to attrition and is capable of producing acrylonitrile with a high degree of yield thereof.

It is a great advantage of the present invention that the catalyst of the present invention exhibits both an excellent resistance to attrition and a superior capability of producing acrylonitrile with a high yield thereof. As stated above, it is not completely clear in what form of a compound each element in the catalyst of the present invention exists. However, from the results of an X-ray diffractiometrical observation and in view of an infrared ray absorption spectrum of the catalyst of the present invention, it is assumed that the elements are in the form of complex compounds in which atoms of a plurality of elements are bonded to an oxygen atom or atoms, for example, cobalt and/or nickel molybdate, iron molybdate, and a compound of molybdenum, bismuth and iron with oxygen. The complex compounds forms, as a whole, the oxide composition of the empirical formula (I).

In the process for producing the catalyst comprising an oxide composition of the empirical formula (I), a molybdenum-containing compound, with at least one member selected from cobalt- and nickel-containing compounds, an iron-containing compound, a bismuth-containing compound, a vanadium-containing compound, a calcium-containing compound, a potassium-containing compound, with at least one member selected from zirconium- and chromium-containing compounds, and silicon-containing compound, each in an amount sufficient to satisfy the above-specified atomic ratio of the elements in the empirical formula (I), are mixed with each other and with an aqueous liquid to prepare an aqueous slurry; the aqueous slurry is spray-dried to prepare a dried solid precursor catalyst, and, finally, the precursor cataypst is calcined at a temperature of from 500° to 750° C. to prepare an activated catalyst.

In the mixing operation, the aqueous liquid may be selected from the group consisting of water and aqueous solutions of nitric acid, preferably, in an amount of from 5 to 30% by weight. The compounds of the respective elements are preferably selected from compounds soluble in water or the nitric acid aqueous solutions. For example, the molybdenum-containing compound may be selected from molybdic acid, ammonium molybdate, molybdenum trioxide, and molybdenum sulfide.

The cobalt-containing compound may be selected from cobalt carbonates, cobalt nitrates, cobalt oxides, cobalt chlorides, cobalt hydroxides, and cobalt sulfides. The nickel-containing compound may be selected from nickel nitrate, nickel carbonate, nickel oxide, nickel oxalate, nickel hydroxide, nickel chloride, nickel acetate and nickel sulfide.

The iron-containing compound may be selected from ferrous nitrate, ferric nitrate, ferrous oxide, ferric oxide, ferrous chloride, ferric chloride, ferrous hydroxide, ferric hydroxide, ferric phosphate, iron sulfides, ferrous sulfate and ferric sulfate.

The bismuth-containing compound may be selected from bismuth chloride, bismuth nitrate, bismuth oxide, bismuth oxychloride, bismuth hydroxide and bismuth subnitrate.

The vanadium-containing compound may be selected from vanadium pentaoxide, vanadium tetrachloride, ammonium metavanadate and vanadyl oxalate.

The calcium-containing compound may be selected from calcium nitrate, calcium carbonate, calcium chloride, calcium hydroxide and calcium oxide.

The potassium-containing compound may be selected from potassium nitrate, potassium carbonate, potassium chloride, potassium hydroxide and potassium oxide.

The zirconium-containing compound may be selected from zirconium nitrate, zirconium oxide nitrate, zirconium oxynitrate, zirconium oxide, zirconium hydroxide, zirconium oxyacetate and zirconium oxychloride.

The chromium-containing compound may be selected from chromium nitrate, chromium nitrate, chromium carbonate, chromium acetate, chromium chloride, chromium hydroxide and chromium oxide.

Also, the silicon-containing compound may be silica sol.

In the process of the present invention, it is preferable that the temperature and pH of the aqueous slurry are adjusted, before the spray drying operation, to a temperature of 60° C. or less, more preferably, from 20° to 60° C. and to a pH of 1.0 or less. The control of the pH of the aqueous slurry can be effected by using a nitric acid aqueous solution. When the value of the pH of the aqueous slurry is larger than 1.0, sometimes, some components in the aqueous slurry might become coagulated. The coagulation prevents the spray drying operation from being carried out smoothly. Even if the spray drying operation for the aqueous slurry having a pH of more than 1.0 could be effected, it would be difficult to obtain a catalyst for practical use having a satisfactory resistance to attrition. Also, the temperature of the aqueous slurry is higher than 60° C., sometimes the stability of the aqueous slurry becomes poor, and the resultant catalyst exhibits a poor degree of yield of acrylonitrile and an unsatisfactory resistance to attrition.

In the process of the present invention, it is necessary that the content of the sum of the respective element-containing compounds, which are in the form of solid particles suspended in the aqueous slurry, be at a level of not more than 15%, preferably, from 5 to 12%, based on the entire weights of the aqueous slurry.

Furthermore, it is necessary that the solid particles in the aqueous slurry have a size of 2 microns or less. This small size of the solid particles is effective for causing a smooth spray drying operation of the aqueous slurry.

The content and size of the solid particles in the aqueous slurry can be determined by the following method. A predetermined weight ($M_1$) of a aqueous slurry is centrifuged to separate the solid particles from the aqueous liquid, and then, the separated solid particles are dried at a temperature of 200° C. The weight ($M_2$) of the dried solid particles is measured.

Content (%) of solid particles = $(M_2/M_1) \times 100$

Also, in order to determine the size of the solid particles, a drop of the aqueous slurry is placed on a glass plate and a microscopic photograph of the slurry drop on the glass plate is taken. Then, the sizes of the solid particles in the photograph are measured.

When the solid particles in the aqueous slurry are more than 15% and larger than 2 microns in size, the composition and size of the spray dried solid particles of the precursor catalyst might be uneven, the calcined catalyst might exhibit a poor resistance to attrition, and the degrees of conversion of propylene and selectivity to acrylonitrile might be poor.

In the spray drying operation in the process of the present invention, it is preferable that the resultant dried fine solid particles of the precursor catalyst have a size in a range of from 20 to 150 microns, and an average size in a range of, from 40 to 80 microns.

The particles of the precursor catalyst may be shaped or not shaped before the calcining operation. The calcining operation is carried out at a temperature of from 500° to 750° C., preferably, from 550° to 700° C., in an oxygen-containing gas atmosphere for a time sufficient to convert the precursor catalyst into an activated catalyst.

When the precursor catalyst particles are directly calcined without applying the shaping operation thereto, it is preferable that the particles of the activated catalyst have a size of from 20 to 150 microns.

In the process of the present invention, it is also important that the spray drying operation is applied to the aqueous slurry to convert it into the precursor catalyst in the form of fine solid particles.

If the catalyst is prepared by another process which includes no spray drying operation, for example, by evaporation-solidifying the aqueous slurry to prepare a solid precursor catalyst, by calcining the solid precursory catalyst, by pulverizing the calcined catalyst to prepare a catalyst in the form of fine solid particles, and, finally, by shaping the catalyst particles to prepare a catalyst in a desired shape, the resultant catalyst has a poorer degree of selectivity to acrylonitrile, a poorer degree of conversion of propylene, and exhibits a poorer resistance of the catalyst to attrition than those catalysts prepared in accordance with the process of the present invention.

The spray drying operation can be carried out by using any type of conventional spray drying apparatus, for example, a rotating disc type or nozzle type spray drying apparatus. By applying the spray drying operation, the aqueous slurry can be converted into fine, solid, substantially spherical particles. The particles of the precursory catalyst are, if necessary, dried, molded into a desired form, or not molded, and, finally, calcined at the above-specified temperature. When the calcining temperature is lower than 500° C., the resultant catalyst causes the degree of selectivity to acrylonitrile to be poor and exhibits a poor resistance to attrition. Also, a calcining temperature higher than 750° C. results in a poor catalyst which causes the degree of conversion of propylene to be poor.

The catalyst of the present invention can be prepared, for example, by the following procedures.

A. Predetermined amounts of ammonium molybdate and ammonium metavanadate are dissolved in a predetermined amount of hot water to produce Solution A.

B. Predetermined amounts of cobalt nitrate, nickel nitrate, iron (III) nitrate, chromium nitrate, calcium nitrate and potassium nitrate are dissolved in a predetermined amount of water or a nitric acid aqueous solution to produce Solution B.

C. A predetermined amount of bismuth nitrate is dissolved in a predetermined amount of nitric acid aqueous solution to produce Solution C.

D. A predetermined amount of silica sol is provided.

E. Solutions A, B and C and the silica sol are mixed together to prepare an aqueous slurry, while the temperature and pH of the aqueous slurry are adjusted to a desired level not exceeding a temperature of 60° C. and a desired level of pH not exceeding 1.0.

The mixing operations of Solutions A, B and C and the silica sol can be effected in any order. However, it is not preferable to mix Solution A directly with the silica sol.

F. If necessary, the aqueous slurry is stirred with, for example, a homogenizer, to adjust the size of the solid particles to a level not exceeding 2 microns.

G. The aqueous slurry is spray dried to prepare a precursor catalyst in the form of fine solid particles.

H. If necessary, the particles of the precursor catalyst are dried.

I. If necessary, the particles of the precursor catalyst are shaped into a desired shape.

J. The precursor catalyst is calcined at a temperature of from 500° to 750° C. to prepare an activated catalyst.

The catalyst of the present invention is effective for ammoxidizing propylene to produce acrylonitrile. The ammoxidation process is preferably carried out at a temperature of from 380° to 500° C., more preferably, from 400° to 470° C.

The ammoxidizing operation is carried out usually under an ambient pressure. However, the ammoxidizing operation may be effected under a slightly reduced pressure. In the ammoxidation operation, a reaction feed gas is brought into contact with the catalyst so that the contact is continued preferably for a time of from 0.5 to 10 seconds, more preferably, from 1 to 8 seconds. The reaction feed gas preferably contains propylene in a concentration of from 1 to 20%, more preferably, from 2 to 10%, by volume, and; molecular oxygen in an amount of from 1 to 4 mole, more preferably, from 1.5 to 3 mole and, ammonia gas in an amount of from 0.7 to 1.5 mole, more preferably, from 0.9 to 1.2 mole, per mole of propylene gas. It is not essential that the molecular oxygen gas and the ammonia gas are highly pure. The molecular oxygen may be mixed with another inert gas so as to form an oxygen-containing gas, for example, air. Usually, it is convenient to use air as an oxygen-containing gas. Also, propylene gas is not required to be highly pure. However, it is undesirable for the propylene gas to contain unsaturated hydrocarbon gases, for example, acetylene, which are highly reactive.

In the ammoxidizing operation, the reaction feed gas may contain an inert gas as a dilute gas, in addition to the oxygen, ammonia and propylene. The dilute gas may be selected from steam, nitrogen gas and carbon dioxide gas, which do not substantially affect the ammoxidation reaction of propylene. The steam is effective for increasing the degree of selectivity to acrylonitrile and for enhancing the durability in catalytic activity of the catalyst. Accordingly, it is preferable that the ammoxidizing operation is carried out in the presence of steam. In this case, the steam is used preferably in an amount of 0.1 to 5 mole, more preferably, from 0.5 to 4 mole, per mole of propylene.

The ammoxidizing operation for propylene in the presence of the catalyst of the present invention can be carried out in any type of reactor, for example, a fixed bed or a fluidized bed type reactor. When the fluidized bed type reactor is used, since the reaction mixture naturally contains steam which has been derived from the ammoxidation of propylene, it is unnecessary to add steam to the reaction feed gas. However, when the fixed bed type reactor is utilized, it is preferably to add steam to the reaction feed gas.

The catalyst of the present invention is not required to be provided with a special form thereof. However, when the catalyst is used in the fixed bed type reactor, it is preferable that the catalyst is shaped to prepare pellets each having a diameter of, for example, 5 mm and a thickness of, for example, 5 mm. However, when the catalyst is used in the fluidized bed type reactor, it is preferable that the catalyst is in the form of fine particles each having a size of from 20 to 150 microns.

After completing the ammoxidating operation, the resultant acrylonitrile can be isolated from the reaction mixture by any conventional isolating method, for example, the methods disclosed in U.S. Pat. Nos. 3,424,781 and 3,688,002.

The specific examples set forth below will serve to more fully explain the practice of the present invention. However, it should be understood that the examples are only illustrative and should in no way limit the scope of the present invention.

In the examples, the percent of conversion of propylene, percent selectivity to acrylonitrile and percent yield of acrylonitrile were respectively calculated in accordance with the following equations.

$$\text{Percent of conversion of propylene} = \frac{X_1 - X_2}{X_1} \times 100$$

$$\text{Percent of selectivity to acrylonitrile} = \frac{Y}{X_1 - X_2} \times 100$$

$$\text{Percent of yield of acrylonitrile} = \frac{Y}{X_1} \times 100$$

wherein:

$X_1$: a molar amount of propylene contained in the reaction feed gas prior to the start of the reaction;

$X_2$: a molar amount of propylene contained in the reaction mixture after the completion of the reaction;

Y: a molar amount of the resulting acrylonitrile.

Also, in the example, the percent of loss of the catalyst due to attrition was determined by the following procedures.

A. When used in a fixed type reactor.

Particles of the catalyst were shaped to prepare pellets each having a diameter of about 5 mm and a thickness of about 5 mm.

A pipe which had an inside diameter of 2.54 cm and a length of 3 m and which was provided with a wire net having a 6 mesh size and placed on the bottom of the pipe, was stood upright.

50 g of the catalyst pellets were put in at the top opening of the pipe and fell toward the bottom of the pipe, so as to allow the catalyst pellets to contact the wire net.

The weight of the catalyst pellets which passed through the wire net, was measured.

$$\text{The percent of attrition loss of the catalyst} = \frac{\text{Weight (g) of catalyst passed through wire net}}{\text{Entire weight (\%) of catalyst}} \times 100$$

B. When used in a fluidized bed type reactor.

The attrition loss of the catalyst in the form of fine particles, each having a size of from 20 to 150 microns, was determined in accordance with the TEST METHODS FOR SYNTHETIC FLUID CRACKING CATALYSTS, Page 43, American Cyanamide Co., 6131-4M-1/57. The percent of attrition loss of the catalyst was calculated in accordance with the equation:

$$\text{Percent of loss} = \frac{B - A}{C - A} \times 100$$

wherein A represented a weight (g) of a portion of catalyst which was lost in the period of 5 hours from the start of the measurement, B represented a weight (g) of a portion of the catalyst lost in the measurement period of 20 hours from the start of the measurement, and C denoted the entire weight (g) of the catalyst subjected to the test.

EXAMPLE 1

Preparation of catalyst suitable for use in a fixed bed type reactor

Solution A: 381.8 g of ammonium molybdate [$(NH_4)_6Mo_7O_{24}.4H_2O$] and 0.25 g of ammonium metavanadate [$NH_4VO_3$] were dissolved in 623 ml of hot water at a temperature of about 50° C.

Solution B: This was prepared by dissolving
125.9 g of Cobalt nitrate [$Co(NO_3)_2.6H_2O$],
251.6 g of nickel nitrate [$Ni(NO_3)_2.6H_2O$],
87.4 g of iron (III) nitrate[$Fe(NO_3)_3.9H_2O$],
86.5 g of chromium nitrate [$Cr(NO_3)_3.9H_2O$],
5.1 g of calcium nitrate [$Ca(NO_3)_2.4H_2O$], and
2.0 g of potassium nitrate [$KNO_3$]

in 492 ml of hot water at a temperature of about 50° C.

Solution C: 58 ml of a 60% nitric acid were dissolved in 314 ml of water and then, 104.9 g of bismuth nitrate [$Bi(NO_3)_3.5H_2O$] and 14.5 g of zirconium oxide nitrate [$ZrO(NO_3)_2.2H_2O$] were dissolved in the nitric acid aqueous solution at a temperature of about 50° C.

Silica sol D: 1667 g of a commercial silica sol which contains 30% by weight of silicon in terms of $SiO_2$, were heated to elevate the temperature thereof to about 50° C.

Solution B was mixed with Solution C, the mixture was added dropwise to Solution A and, finally, Silica sol D was mixted to the admixture of Solutions A, B and C, to prepare an aqueous slurry. The resulting aqueous slurry exhibited a temperature of about 50° C. After vigorously stirring the aqueous slurry with a homogenizer to pulverize the solid components in the slurry, the resultant aqeuous slurry exhibited a temperature of 30° C. and a pH of less than 1.0 and contained 9.4% by weight of the pulverized solid particles, each having a size of about 1.8 microns or less.

The aqueous slurry was spray dried with a rotating disc type spray drying apparatus to prepare fine solid particles having an average size of about 50 microns. The particles of the resulting percursory catalyst were shaped by using a tablet shaping machine to prepare rod-shaped tablets, each having a diameter of 5 mm and a length of 5 mm. The tablets were calcined in air at a temperature of 575° C. for 5 hours to prepare activated catalyst tablets suitable for the fixed bed ammoxidation of propylene.

The atomic ratio of the elements in the resultant catalyst, except for oxygen, is indicated below.

$Mo_{10}Co_2Ni_4Fe_1Cr_1Ca_{0.1}K_{0.1}Zr_{0.25}Bi_1V_{0.01}Si_{37.3}$

The results of the attrition test of the catalyst revealed that the loss due to attrition was 0.02%.

AMMOXIDATION OF PROPYLENE IN A FIXED BED TYPE REACTOR

The above-prepared catalyst was crushed and 8 ml of the crushed catalyst was placed in a U-shaped glass reactor having an inside diameter of 8 mm. A reaction feed gas consisting of a mixture of propylene, ammonia, air and steam in a molar ratio of 1:1:11:2, was allowed to flow at a rate of 282 ml/min through the reactor, so as to bring the reaction feed gas into contact with the catalyst at a temperature of 420° C. for a contact time of 1.7 seconds.

One hour after the start of the reaction, it was found that the conversion of propylene was 94.8%, the selectivity to acrylonitrile was 86.3% and the yield of acrylonitrile was 84.9%.

EXAMPLES 2 THROUGH 6

In each of the Examples 2 through 6, the same procedures as those described in Example 1 were carried out, except that the aqueous slurry was prepared at the temperature indicated in Table 1, and contained the solid particles in the amount indicated in Table 1 and the solid particles in the aqueous slurry had an average size as indicated in Table 1. Also, it was confirmed that the pH of the aqueous slurry was 1.0 or less.

The resultant catalyst exhibited a loss due to attrition as indicated in Table 1.

Also, when the catalyst was used in the fixed bed type reactor, the results of the ammoxidation of propylene were as indicated in Table 1.

EXAMPLES 7 AND 8

In each of the Examples 7 and 8, the same procedures as those described in Example 1 were carried out, except that the calcining operation was carried out at a temperature as indicated in Table 1. The results of the attrition test applied to the resultant catalyst and of the ammoxidation of propylene in the presence of the resultant catalyst are also indicated in Table 1.

EXAMPLE 9

The same procedures as those described in Example 1 were carried out, except that the aqueous slurry was prepared by mixing Solution B with Solution C and, then, with silica sol D and, finally, by adding Solution A to the above-prepared mixture. It was confirmed that the resultant aqueous slurry exhibited a pH of 1.0 or less.

The results of the attrition test applied to the resultant catalyst and of the ammoxidation of propylene in the presence of the resultant catalyst are also indicated in Table 1.

EXAMPLES 10 THROUGH 25

In each of the Examples 10 through 25, the same procedures as those described in Example 1 were carried out, except that the preparation of the aqueous slurry was carried out at a temperature of 50° C., the resultant catalyst had an atomic ratio of the elements therein as indicated in Table 2, the aqueous slurry contained solid particles in an amount indicated in Table 2 and the average size of the solid particles was as indicated in Table 2.

The results of the attrition test applied to the resultant catalyst and of the ammoxidation of propylene in the presence of the catalyst are shown in Table 3.

TABLE 2

| Example No. | Atomic ratio of elements in catalyst | | | | | | | | | | | Content of solid particles in aqueous slurry (%) by weight | Average size of solid particles in aqueous slurry (micron) |
|---|---|---|---|---|---|---|---|---|---|---|---|---|---|
| | Mo | Co | Ni | Fe | Bi | V | Ca | K | Zr | Cr | Si | | |
| 10 | 10 | 3 | 3 | 1 | 1 | 0.01 | 0.1 | 0.1 | 0.25 | 1 | 37.3 | 9.5 | 2.0 |
| 11 | 10 | 4 | 2 | 1 | 1 | 0.01 | 0.1 | 0.1 | 0.25 | 1 | 37.3 | 9.6 | 1.8 |
| 12 | 10 | 2 | 4 | 1.5 | 1 | 0.01 | 0.1 | 0.1 | 0.25 | 0.5 | 37.3 | 9.6 | 1.9 |
| 13 | 10 | 3 | 3 | 2 | 1.5 | 0.01 | 0.4 | 0.1 | 0.3 | 0.7 | 37.3 | 10.1 | 2.0 |
| 14 | 10 | 2 | 4 | 1 | 1 | 0.01 | 0.1 | 0.1 | 0.25 | 1 | 30.5 | 9.2 | 1.8 |
| 15 | 10 | 2 | 4 | 1 | 1 | 0.01 | 0.1 | 0.1 | 0.25 | 1 | 25 | 10.7 | 1.6 |
| 16 | 10 | 2 | 4 | 1 | 1 | 0.01 | 0.1 | 0.1 | 0.25 | 1 | 16 | 11.6 | 1.5 |
| 17 | 10 | 2 | 4 | 0.5 | 1 | 0.1 | 1 | 0.15 | 0.4 | 1.5 | 25 | 10.8 | 1.8 |
| 18 | 10 | 3 | 4 | 0.7 | 0.7 | 0.02 | 0.5 | 0.1 | 0.2 | 0.5 | 37.5 | 9.4 | 1.7 |
| 19 | 10 | 2 | 4 | 1 | 0.9 | 0.1 | 0.1 | 0.2 | 0.6 | 0.8 | 30.5 | 9.1 | 1.6 |
| 20 | 10 | 3 | 5 | 0.9 | 1 | 0.05 | 2 | 0.1 | 0.3 | 1 | 16 | 11.3 | 1.5 |
| 21 | 10 | 6 | 0 | 1 | 1 | 0.01 | 0.1 | 0.1 | 0.25 | 1 | 37.3 | 9.8 | 1.8 |
| 22 | 10 | 0 | 6 | 1 | 1 | 0.01 | 0.1 | 0.1 | 0.25 | 1 | 37.3 | 9.5 | 1.7 |
| 23 | 10 | 0 | 6 | 1 | 1 | 0.01 | 0.1 | 0.1 | 0 | 1 | 37.5 | 10.3 | 1.9 |
| 24 | 10 | 0 | 6 | 1 | 1 | 0.01 | 0.1 | 0.1 | 0.25 | 0 | 37.5 | 10.4 | 1.8 |
| 25 | 10 | 0 | 6 | 1 | 1 | 0.01 | 0.1 | 0.1 | 0 | 0 | 37.5 | 10.1 | 1.9 |

TABLE 3

| Example No. | Loss due to attrition (%) | Conversion of propylene (%) | Selectivity to acrilonitrile (%) | Yield of acrylonitrile (%) |
|---|---|---|---|---|
| 10 | 0.01 | 96.8 | 85.4 | 82.7 |
| 11 | 0.03 | 97.5 | 84.9 | 82.8 |
| 12 | 0.02 | 98.5 | 85.6 | 84.3 |
| 13 | 0.02 | 97.5 | 84.3 | 82.2 |
| 14 | 0.04 | 98.5 | 85.2 | 83.9 |
| 15 | 0.05 | 98.6 | 86.0 | 84.8 |
| 16 | 0.06 | 98.8 | 85.9 | 84.9 |
| 17 | 0.05 | 99.0 | 84.6 | 83.8 |
| 18 | 0.01 | 97.8 | 85.1 | 83.2 |
| 19 | 0.04 | 96.5 | 85.8 | 82.8 |
| 20 | 0.06 | 97.7 | 85.7 | 83.7 |
| 21 | 0.02 | 96.8 | 86.5 | 83.7 |

TABLE 1

| Example No. | Temperature (°C.) in aqueous slurry-preparing operation | Content of solid particles in aqueous slurry (%) by weight | Average size of solid particles in aqueous slurry (micron) | Calcining Temperature (°C.) | Loss due to attrition (%) | Conversion of propylene (%) | Selectivity to acrylonitrile (%) | Yield of acrylonitrile (%) |
|---|---|---|---|---|---|---|---|---|
| 1 | 50 | 9.4 | 1.8 | 575 | 0.02 | 98.4 | 86.3 | 84.9 |
| 2 | 40 | 8.5 | 1.8 | 575 | 0.01 | 97.9 | 86.4 | 84.6 |
| 3 | 60 | 10.2 | 1.9 | 575 | 0.01 | 96.8 | 85.8 | 83.1 |
| 4 | 50 | 9.3 | 1.7 | 575 | 0.02 | 95.6 | 85.9 | 82.1 |
| 5 | 50 | 7.0 | 1.1 | 575 | 0.01 | 97.2 | 86.3 | 83.9 |
| 6 | 50 | 12.0 | 2.0 | 575 | 0.03 | 97.5 | 86.5 | 84.3 |
| 7 | 50 | 9.4 | 1.8 | 550 | 0.04 | 98.1 | 85.1 | 83.5 |
| 8 | 50 | 9.4 | 1.8 | 600 | 0.01 | 94.9 | 86.9 | 82.5 |
| 9 | 50 | 9.4 | 1.8 | 575 | 0.02 | 97.5 | 85.8 | 83.7 |

Composition of catalyst (except for oxygen) : $Mo_{10}Co_2Ni_4Fe_1Bi_1V_{0.01}Ca_{0.1}K_{0.1}Zr_{0.25}Cr_1Si_{37.3}$
Ammoxidation temperature: 420° C.
Contact time: 1.7 seconds TABLE 3-continued

| Example No. | Loss due to attrition (%) | Conversion of propylene (%) | Selectivity to acrilonitrile (%) | Yield of acrylonitrile (%) |
|---|---|---|---|---|
| 22 | 0.04 | 98.8 | 85.9 | 84.9 |
| 23 | 0.03 | 99.8 | 84.5 | 84.3 |
| 24 | 0.03 | 98.9 | 84.9 | 84.0 |
| 25 | 0.04 | 99.0 | 84.0 | 83.2 |

COMPARISON EXAMPLES 1 THROUGH 13

In each of the Comparison Examples 1 through 13, the same procedures as those described in Example 1 were carried out, except that the preparation of the aqueous slurry was carried out at a temperature of 50° C., the content and size of the solid particles in the aqueous slurry were those indicated in Table 4, respectively, and the resultant catalyst exhibited an atomic ratio of the elements therein, as indicated in Table 4. The atomic ratio fells outside the scope of the present invention.

The results of the attrition test applied to the resultant catalyst and of the ammoxidation of propylene in the presence of the catalyst are shown in Table 5.

COMPARISON EXAMPLE 14

The same procedures as those described in Example 1 were carried out, except that 5.6 g of ammonium paratungstate were used in place of the potassium nitrate, and the resultant catalyst exhibited the atomic ratio of the elements therein indicated in Table 4. The preparation of the aqueous slurry was carried out at a temperature of 50° C., the resultant slurry exhibited a pH not exceeding 1.0, and the calcination was carried out at a temperature of 575° C. The content and average size of the solid particles in the aqueous slurry are as indicated in Table 4.

The results of the attrition test of the resultant catalyst and of the ammoxidation of propylene in the presence of the resultant catalyst, are indicated in Table 5.

TABLE 5

| Comparative Example No. | Loss due to attrition (%) | Conversion of propylene (%) | Selectivity to acrylonitrile (%) | Yield of acrylonitrile (%) |
|---|---|---|---|---|
| 1 | 0.22 | 90.8 | 78.8 | 71.6 |
| 2 | 0.06 | 98.8 | 75.3 | 74.4 |
| 3 | 0.05 | 92.0 | 74.3 | 68.4 |
| 4 | 0.53 | 91.3 | 63.6 | 58.1 |
| 5 | 0.10 | 85.6 | 65.3 | 55.9 |
| 6 | 0.32 | 93.6 | 82.1 | 76.8 |
| 7 | 0.06 | 76.5 | 65.3 | 50.0 |
| 8 | 0.01 | 75.2 | 71.3 | 53.6 |
| 9 | 0.15 | 96.5 | 62.1 | 59.9 |
| 10 | 0.05 | 65.3 | 83.5 | 54.5 |
| 11 | 2.15 | 98.5 | 75.6 | 74.5 |
| 12 | 0.50 | 94.5 | 84.6 | 79.9 |
| 13 | 0.05 | 91.6 | 84.9 | 77.7 |
| 14 | 0.06 | 95.3 | 75.3 | 71.8 |

EXAMPLE 26

Preparation of catalyst suitable for use in a fluidized bed type reactor.

Solution A: This solution was prepared by dissolving 381.8 g of ammonium molybdate [$(NH_4)_6Mo_7O_{24}.4H_2O$] and 0.5 g of ammonium metavanadate [$NH_4VO_3$] in 700 ml of hot water at a temperature of about 45° C.

Solution B: This solution was prepared by dissolving
125.9 g of cobalt nitrate [$Co(NO_3)_2.6H_2O$],
251.6 g of nickel nitrate [$Ni(NO_3)_2.6H_2O$],
86.5 g of chromium nitrate [$Cr(NO_3)_3.9H_2O$],
10.2 g of calcium nitrate [$Ca(NO_3)_2.4H_2O$],
87.4 g of iron (III) nitrate [$Fe(NO_3)_3.9H_2O$]
and 2.0 g of potassium nitrate [$KNO_3$] in
500 ml of hot water at a temperature of about 45° C.

Solution C: This solution was prepared by dissolving 80 ml of a 60% nitric acid in 320 ml of water; adding 104.9 g of bismuth nitrate [$Bi(NO_3)_3.5H_2O$] to the above-prepared nitric acid solution and, finally, heating the admixture to a temperature of about 30° C.

Silica sol D: 1667 g of a silica sol which contained silicon in an amount of 30% by weight in terms of $SiO_2$, were heated to a temperature of about 30° C.

Solution B was mixed with Solution C and, then, with Solution A while stirring the mixture, and finally, Silica sol D was mixed to the above-prepared mixture to prepare an aqueous slurry. This slurry had a temperature of

TABLE 4

| Comparative Example No. | Atomic ratio of elements in catalyst | | | | | | | | | | | Content of solid particles in aqueous slurry (%) by weight | Average size of solid particles in aqueous slurry (micron) |
|---|---|---|---|---|---|---|---|---|---|---|---|---|---|
| | Mo | Co | Ni | Fe | Bi | V | Ca | K | Zr | Cr | Si | | |
| 1 | 10 | 6 | 0 | 1 | 1 | 0 | 0 | 0.07 | 0.25 | 0 | 37.3 | 11.5 | 2.3 |
| 2 | 10 | 10 | 0 | 1 | 1 | 0.01 | 0.1 | 0.1 | 0.25 | 1 | 37.3 | 12.2 | 2.1 |
| 3 | 10 | 2 | 4 | 0.1 | 1 | 0.01 | 0.1 | 0.1 | 0.40 | 1 | 37.3 | 11.3 | 2.2 |
| 4 | 10 | 2 | 4 | 1 | 4 | 0.01 | 0.2 | 0.1 | 0.25 | 1 | 37.3 | 16.0 | 3.2 |
| 5 | 10 | 3 | 3 | 1.2 | 1 | 0.01 | 0.1 | 0.1 | 0.25 | 3 | 37.3 | 10.9 | 2.4 |
| 6 | 10 | 4 | 2 | 1 | 0.8 | 0.01 | 0 | 0.1 | 0.25 | 0.5 | 37.3 | 11.3 | 2.5 |
| 7 | 10 | 2 | 4 | 1 | 1 | 0 | 7 | 0 | 0.25 | 1 | 37.3 | 14.2 | 3.5 |
| 8 | 10 | 2 | 4 | 1 | 1 | 0 | 0.5 | 0 | 0.25 | 1 | 55.9 | 8.2 | 1.2 |
| 9 | 10 | 2 | 4 | 1 | 1 | 3 | 0.5 | 0.1 | 0.25 | 1 | 37.3 | 11.5 | 3.2 |
| 10 | 10 | 2 | 4 | 1 | 1 | 0.1 | 0.5 | 1 | 0.25 | 1 | 37.3 | 10.2 | 2.1 |
| 11 | 10 | 2 | 4 | 1 | 1 | 0 | 0.1 | 0 | 0.25 | 1 | 0 | 16.2 | 2.6 |
| 12 | 10 | 2 | 4 | 1 | 1 | 0 | 0.1 | 0.1 | 0.25 | 1 | 5 | 13.2 | 2.1 |
| 13 | 10 | 2 | 4 | 1 | 1 | 0 | 0.1 | 0.1 | 0.25 | 1 | 37.3 | 10.6 | 1.9 |
| 14 | 10 | 2 | 4 | 1 | 1 | 0.01 | 0.1 | K = 0, W = 0.1 | 0.25 | 1 | 37.3 | 11.2 | 2.1 | about 44° C. The aqueous slurry was vigorously stirred with a homogenizer for minutes to pulverize the solid components in the slurry. The stirred aqueous slurry exhibited a temperature of 30° C., a pH not exceeding 1.0, a content of solid particles of 8% by weight and a size of the pulverized solid particles of 1.7 microns or less.

The aqueous slurry was spray dried with a rotating disc type atomization drying apparatus to prepare a precursory catalyst in the form of fine particles having a size of from 20 to 150 microns. The precursory catalyst particles were directly calcined in an air atmosphere at a temperature of 650° C. for 5 hours to prepare an activated catalyst suitable for use in a fluidized bed type reactor. The catalyst particles exhibited an average size of 55 microns and an atomic ratio of the elements therein, except for oxygen, as indicated below.

$$Mo_{10}Co_2Ni_4Fe_1Cr_1Ca_{0.2}K_{0.1}Bi_1Si_{37.3}V_{0.02}$$

The attrition test applied to the catalyst revealed that the loss due to abrasion was 0.46%.

AMMOXIDATION OF PROPYLENE IN A FLUIDIZED BED TYPE REACTOR 150 ml of the catalyst particles were placed in a fluidized bed type reactor having an inside diameter of 36 mm. A reaction feed gas consisting of a mixture of propylene, ammonia, air and steam in a molar mixing ratio of 1:1.14:12.1:1, was allowed to flow at a rate of 2571 ml/min through the reactor at a temperature of 430° C., so as to bring the reaction feed gas into contact with the catalyst in a contact time of 3.5 seconds.

The results of the ammoxidation exhibited that the conversion of propylene was 98.0%, the selectivity to acrylonitrile was 85.9% and the yield of acrylonitrile was 84.2%.

We claim:

1. A catalyst for producing acrylonitrile by the catalytic ammoxidation of propylene, said catalyst comprising an oxide composition of the empirical formula (I):

$$Mo_aCo_bNi_cFe_dBi_eV_fCa_gK_hX_iSi_jO_k \qquad (I)$$

wherein X represents at least one element selected from the group consisting of zirconium and chromium, the subscripts a, b, c, d, e, f, g, h, i and j respectively denote the number of the respective atoms of the elements, and the ratio a:b:c:d:e:f:g:h:i:j is in a range of 10:0 to 8:0 to 8:0.3 to 7:0.01 to 3:0.01 to 2:0.01 to 5:0.05 to 0.5:0 to 2:10 to 50, the ratio a:(b+c) being in a range of 10:2 to 10, and the subscript k denotes the number of oxygen atoms which satisfies the average valency of the elements other than oxygen, the ratio a:k being in a range of 10:30 to 80, and said catalyst is prepared by (a) mixing an aqueous liquid with (1) a molybdenum-containing compound, (2) at least one member selected from cobalt- and nickel-containing compounds, (3) an iron-containing compound, (4) a bismuth-containing compound, (5) a vanadium-containing compound, (6) a calcium-containing compound, (7) a potassium-containing compound, (8) at least one member selected from zirconium- and chromium-containing compounds, and (9) a silicon-containing compound, each in an amount sufficient to satisfy the abovespecified atomic ratio of the elements in the empirical formula (I), to prepare an aqueous slurry, said aqueous slurry containing not more than 15% of the sum of the respective element-containing compounds, which are in the form of solid particles having a size of 2 microns or less, based on the entire weight of said aqueous slurry, and having a pH of 1.0 or less;

(b) spray drying said aqueous slurry to form a dried solid precursor catalyst, and (c) calcining said precursor catalyst at a temperature of from 500° to 750° C. to prepare an activated catalyst.

2. A catalyst as claimed in claim 1, wherein the ratio a:b:c:d:e:f:g:h:i:j is in a range of 10:0 to 8:0 to 8:0.5 to 5:0.03 to 2:0.01 to 1:0.05 to 4:0.07 to 0.4:0.1 to 1.9:15 to 45 and the ratio a:(b+c) is in a range of 10:3 to 9.

3. A catalyst as claimed in claim 1, wherein said catalyst is in the form of fine particles having a size of from 20 to 150 microns.

4. A process for producing an ammoxidation catalyst comprising an oxide composition of the empirical formula (I):

$$Mo_aCo_bNi_cFe_dBi_eV_fCa_gK_hX_iSi_jO_k \qquad (I)$$

wherein X represents at least one element selected from the group consisting of zirconium and chromium, the subscripts a, b, c, d, e, f, g, h, i and j respectively denote the number of the respective atoms of the elements, and the ratio a:b:c:d:e:f:g:h:i:j is in a range of 10:0 to 8:0 to 8:0.3 to 7:0.01 to 3:0.01 to 2:0.01 to 5:0.05 to 0.5:0 to 2:10 to 50, the ratio a:(b+c) being in a range of 10:2 to 10, and the subscript k denotes the number of oxygen atoms which satisfies the average valency of the elements other than oxygen, the ratio a:k being in a range of 10:30 to 80, which process comprises the steps of:

(a) mixing an aqueous liquid with (1) a molybdenum-containing compound, with (2) at least one member selected from the group consisting of cobalt- and nickel-containing compounds, an (3) iron-containing compound, (4) a bismuth-containing compound, (5) a vanadium-containing compound, (6) a calcium-containing compound, (7) a potassium-containing compound, (8) at least one member selected from the group consisting of zirconium- and chromium-containing compounds, and (9) a silicon-containing compound, each in an amount sufficient to satisfy the above-specified atomic ratio of the elements in the empirical formula (I), to prepare an aqueous slurry, said aqueous slurry containing not more than 15% of the sum of the respective element-containing compounds which are in the form of solid particles having a size of 2 microns or less, based on the entire weight of said aqueous slurry, and having a pH of 1.0 or less;

(b) spray drying said aqueous slurry to form a dried solid precursor catalyst, and (c) calcining said precursor catalyst at a temperature of from 500° to 750° C. to prepare an activated catalyst.

5. A process as claimed in claim 4, wherein said precursor catalyst is shaped into a desired form before said calcining.

6. A process as claimed in claim 4, wherein said aqueous liquid is selected from the group consisting of water and nitric acid aqueous solutions.

7. A process as claimed in claim 4, wherein said aqueous slurry has a temperature of 60° C. or less.

8. A process as claimed in claim 4, wherein the amount of said solid particles in said aqueous slurry is in a range of from 5 to 12% based on the entire weight of said aqueous slurry.

* * * * *